United States Patent [19]
van Lintel

[11] Patent Number: 5,271,724
[45] Date of Patent: Dec. 21, 1993

[54] VALVE EQUIPPED WITH A POSITION DETECTOR AND A MICROPUMP INCORPORATING SAID VALVE

[75] Inventor: Harald T. G. van Lintel, Enschede, Netherlands

[73] Assignee: Westonbridge International Limited, Dublin, Ireland

[21] Appl. No.: 848,985

[22] PCT Filed: Aug. 21, 1991

[86] PCT No.: PCT/EP91/01586
§ 371 Date: Apr. 21, 1992
§ 102(e) Date: Apr. 21, 1992

[87] PCT Pub. No.: WO92/04569
PCT Pub. Date: Mar. 19, 1992

[30] Foreign Application Priority Data
Aug. 31, 1990 [CH] Switzerland ............ 02833/90
Feb. 6, 1991 [CH] Switzerland ............ 00360/91

[51] Int. Cl.⁵ ................................ F04B 17/00
[52] U.S. Cl. ..................... 417/413 A; 417/413 B
[58] Field of Search ............ 417/322, 410, 413; 137/855, 859, 554; 200/61.45 R, 61.48, 83 N, 181

[56] References Cited

U.S. PATENT DOCUMENTS

| | | | |
|---|---|---|---|
| 4,543,457 | 9/1985 | Petersen et al. ............ | 200/83 N |
| 4,562,741 | 1/1986 | Hosterman .................. | 73/714 |
| 4,579,001 | 4/1986 | Hosterman .................. | 73/714 |
| 4,585,209 | 4/1986 | Aine et al. .................. | 251/129.02 |
| 4,737,660 | 4/1988 | Allen et al. .................. | 200/61.45 R |
| 4,838,887 | 6/1989 | Idriss .......................... | 604/891.1 |
| 4,855,544 | 8/1989 | Glenn ......................... | 200/61.48 |
| 4,965,415 | 10/1990 | Young et al. ............... | 200/83 N |
| 5,029,805 | 7/1991 | Albarda et al. ............. | 251/11 |
| 5,085,562 | 2/1992 | van Lintel .................. | 417/413 |

FOREIGN PATENT DOCUMENTS

| | | |
|---|---|---|
| 0339528 | 11/1989 | European Pat. Off. |
| 0387439 | 9/1999 | European Pat. Off. |
| 2639085 | 5/1990 | France |

OTHER PUBLICATIONS

Article entitled "A piezoelectric micropump based on micromachining of silicon" *Sensors and Actuators*, No. 15, pp. 153-167, 1988, by Harald T. G. van Lintel.

Primary Examiner—Richard A. Bertsch
Assistant Examiner—Alfred Basichas
Attorney, Agent, or Firm—Pollock, Vande Sande & Priddy

[57] ABSTRACT

A valve is formed from a silicon wafer (20) and has a position detector to detect by contact the position of the valve and hence reveal any malfunction. The position detector comprises a first electrical contact (54) formed on a glass support (32) mounted on the back face of the wafer (20), a second electrical contact fixed to the wafer (20) and an electrical impedance measurement circuit (resistance or capacitance according to the embodiment) between the two electrical contacts. The valve is useful in a micropump for the injection of medicaments.

23 Claims, 4 Drawing Sheets

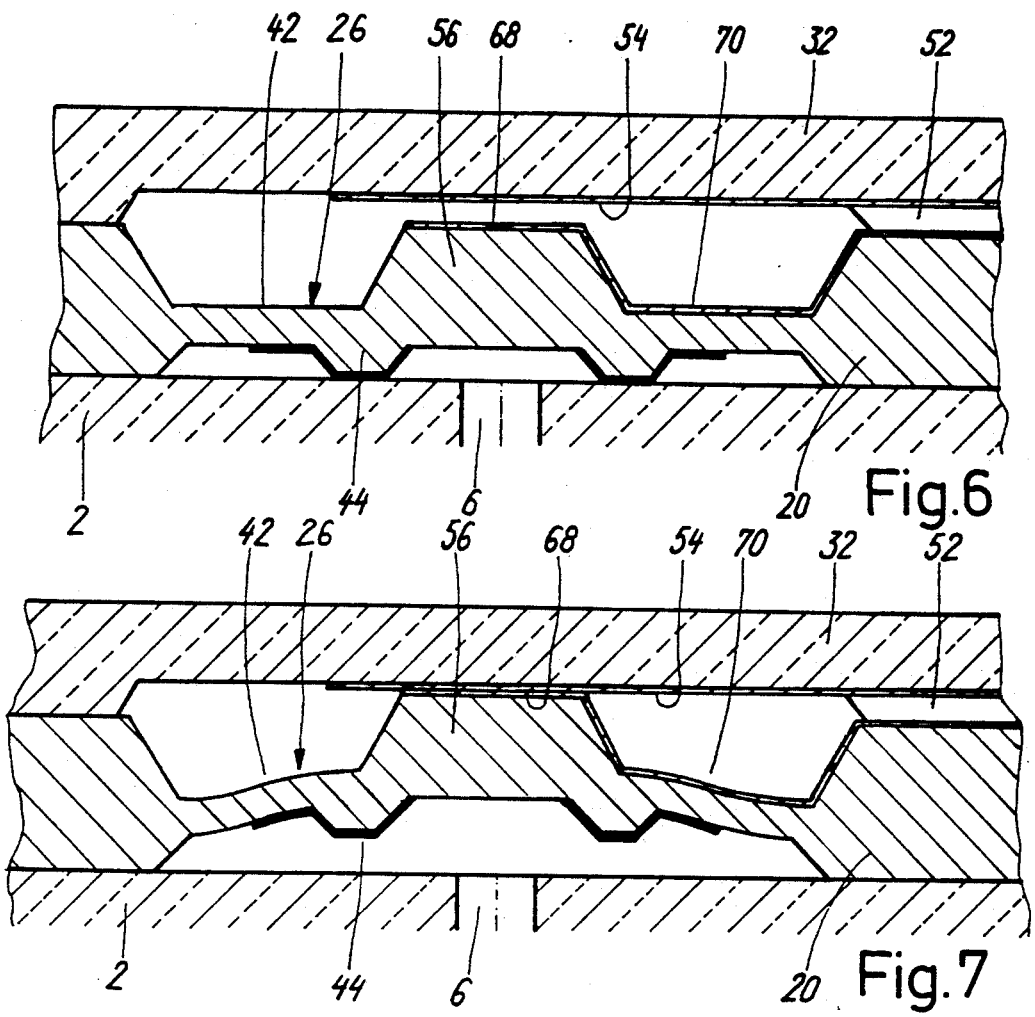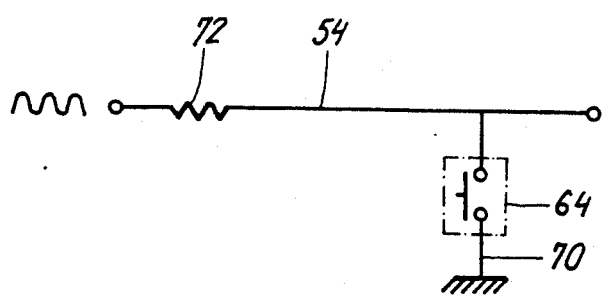

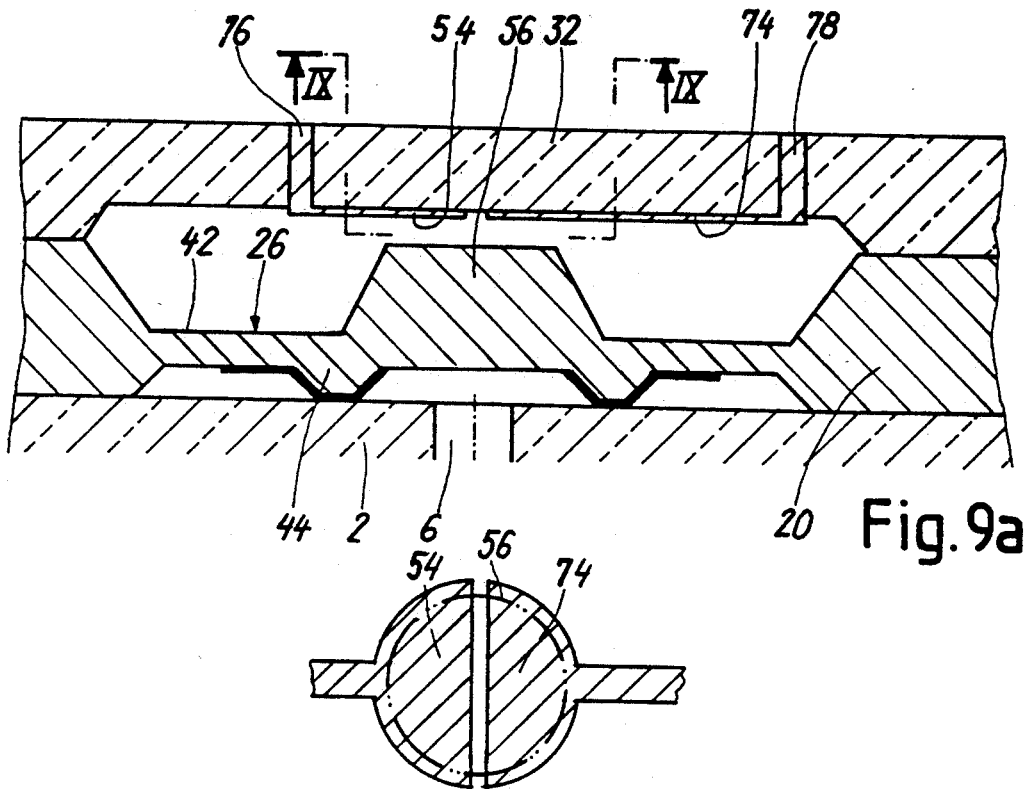
Fig. 9a
Fig. 9b
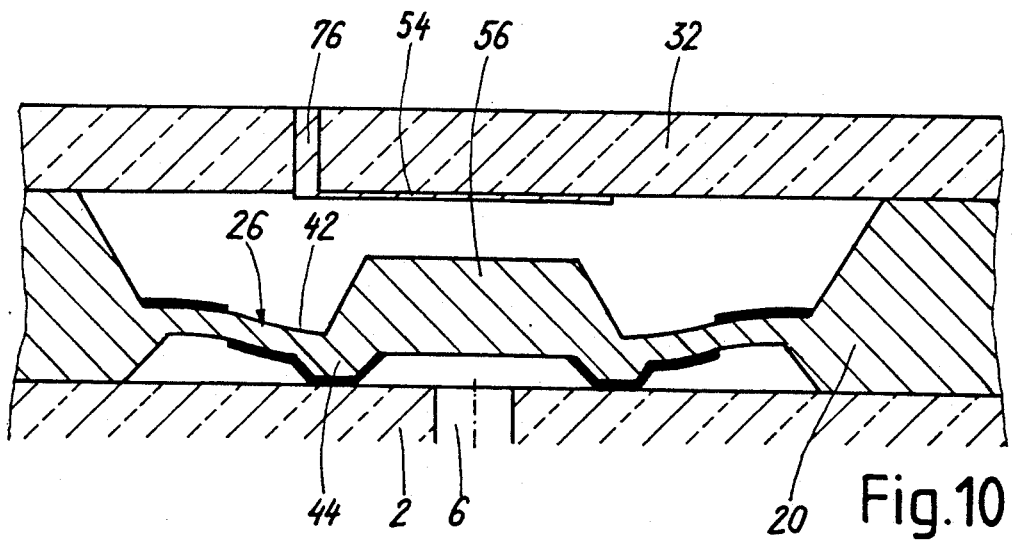
Fig. 10

VALVE EQUIPPED WITH A POSITION DETECTOR AND A MICROPUMP INCORPORATING SAID VALVE

TECHNICAL FIELD

The present invention relates to a valve equipped with a position detector of the type in which the body of the valve is formed by machining a silicon plate by such micromachining techniques as photolithographic technology or similar technologies and a micropump incorporating such a valve.

BACKGROUND OF THE INVENTION

These micropumps may be used notably for the in situ administration of medicaments, the miniaturization of the micropump optionally permitting the permanent implantation thereof into the body. These pumps enable a precise dosage of small quantities of fluids to be injected.

These micropumps are in particular described in the article "A piezoelectric micropump base on micromachining of silicon" by H. van Lintel et al. which appeared in "Sensors and Actuators", No 15, 1988, pages 153-167. These pumps essentially comprise a stack of three wafers, i.e. is a silicon wafer disposed between two glass wafers.

The silicon wafer is etched in order to form a cavity which together with one of the glass wafers defines a pump chamber, an inlet valve and an outlet valve, communicating the pump chamber respectively with an inlet channel and an outlet channel, and a regulating valve. A control element, e.g. a piezoelectric disc, is provided on one wall of the chamber. This piezoelectric disc may by deformed when it is subjected to an electrical voltage which causes deformation of the wall of the pump chamber and hence variation in the volume thereof.

The micropump functions as follows. At rest the inlet and outlet valves are in the closed position. When an electrical voltage is applied the wall of the pump chamber deforms and the pressure increases therein until the outlet valve opens. The fluid contained in the pump chamber is then driven towards the outlet channel. During this phase the inlet valve is held closed by the pressure prevailing in the pump chamber. When, however, the electrical potential is removed or reversed, the pressure therein diminishes. This causes closure of the outlet valve and opening of the entry valve. Fluid is thereby drawn into the pump chamber.

As already indicated above, these micropumps are useful especially for the administration of medicaments. It is therefore important to be able to monitor the correct functioning of these micropumps. Moreover in some cases the pump flow rate may drop considerably, e.g. when bubbles of air are present in the pump chamber, or when the pressure in the exit channel becomes too high.

SUMMARY OF THE INVENTION

Obviously, such malfunctioning should be detected. It has been noted that the movement of a valve might be used for such a purpose. Therefore, an object of the present invention is to provide a valve having a position detector which is, in addition, simple, viable and inexpensive.

More specifically, it is an object of the invention to provide a valve comprising a first wafer and a second wafer bonded to the first wafer to define the valve seat, which is characterized in that it comprises a position detector having a first electrical contact facing the back face of the valve body at such a distance that there is a mechanical contact between the valve body and the first electrical contact when the valve is in the open position, a second electrical contact so that is forms an electrical impedance with said first electrical contact, influenced by said mechanical contact, and a detection circuit sensitive to the electrical impedance between said electrical contacts.

The mechanical contact between the valve body and the first electrical contact thus ensures the largest possible electrical impedance difference between the open and closed positions of the valve.

It is also an object of the invention to provide a micropump equipped with such a position detector.

The characteristic features and advantages of the invention are better illustrated by the following description give for purpose of example, but which is not limiting and with reference to the accompanying drawings in which

BRIEF DESCRIPTION OF THE DRAWINGS

FIG. 8 is a schematic representation of a detection circuit suitable for use with the valve of FIGS. 6 and 7, FIG. 9a shows in section a valve according to a third embodiment of the invention, and FIG. 9b is a top view along line IX—IX of FIG. 9a, and FIG. 10 shows in section a valve according to a fourth embodiment of the invention.

DETAILED DESCRIPTION OF THE INVENTION

Figure 1:
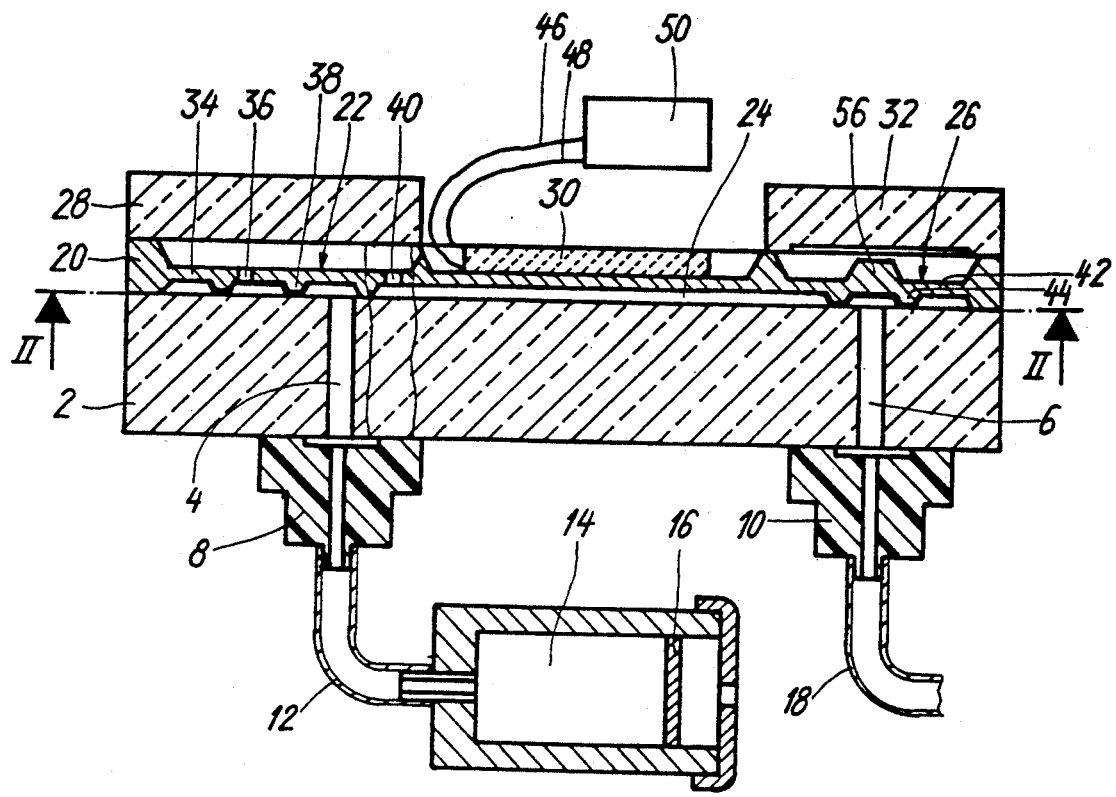
FIG. 1 shows a schematic cross-section along the line I—I of a micropump having a valve according to the invention.
Figure 2:
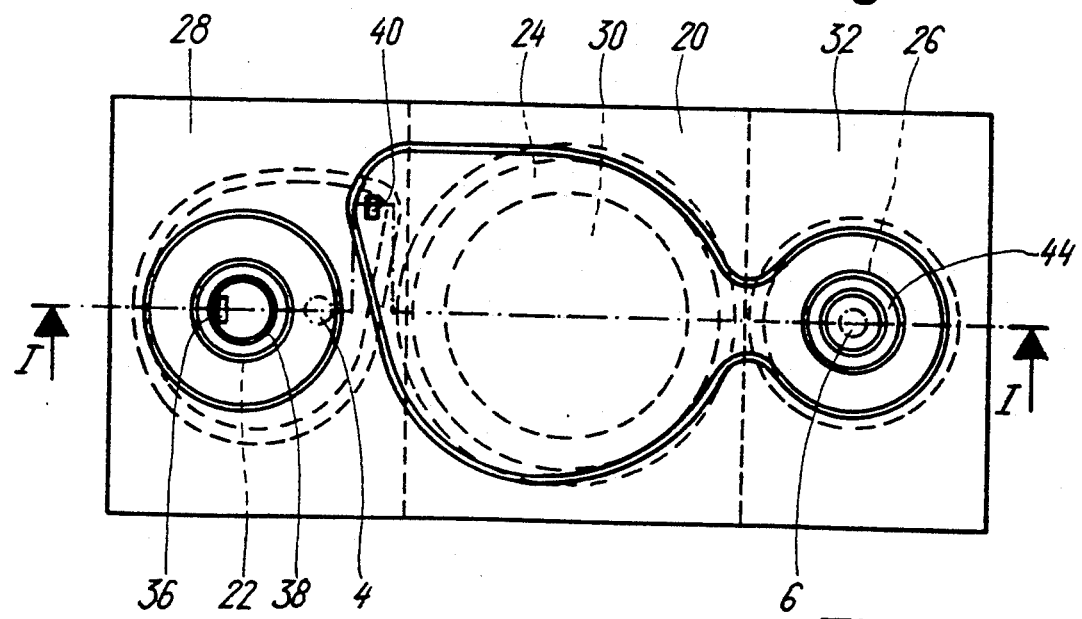
FIG. 2 is a top view along the line II—II of the intermediate wafer of the micropump shown in FIG. 1.

Reference is made first of all to FIGS. 1 and 2 which show a micropump having a valve according to the invention.

It should be noted that for the sake of clarity the thicknesses of the various wafers in the micropumps have been greatly exaggerated in the drawings.

This micropump has a base wafer 2 of for example glass which is pierced by two channels 4 and 6 which constitute the inlet and outlet channels respectively of the pump. These channels communicate respectively with the connectors 8 and 10.

The connector 8 leads to a tube 12 which is itself joined to a reservoir 14 containing the liquid substance to be pumped. The reservoir is sealed by a pierced cap and a movable piston 16 isolating the useful volume of the reservoir 14 from the exterior. This reservoir may contain a medicament, for example in the situation where the pump is to be used to inject a precise dosage of this medicament into the human body. In this application the micropump may be carried on the patient's body or may be implanted.

The outlet connector 10 may be connected to an injection needle (not shown) which is connected thereto by a tube 18. The use in this manner of the micropump is particularly suitable for treating certain forms of cancer with peptides, where medication is preferably given in a precise dosage at regular intervals in small amounts. Another possible application is the injection of insulin for the treatment of diabetics.

A wafer 20 of silicon or any other material capable of being etched by photolithographic technology is bonded to the glass wafer 2. This wafer 20 is machined so as to form an inlet valve 22, a pump chamber 24 and an outlet valve 26 (which forms the regulating valve). A glass sealing wafer 28 is bonded to the wafer 20 above the inlet valve 22, a piezolectric disc 30 to the wall of the pump chamber 24 and a glass support 32 above the outlet valve.

The inlet valve 22 comprises a membrane 34 of substantially circular form with near its center an orifice 36 and, adjacent to the side of an inlet channel 4, an annular sealing ring 38. This latter is covered with a thin oxide layer which confers on the membrane 34 a certain pre-constraint tending to press the sealing ring towards the glass wafer 2, this latter thereby serving as the valve seat 22. When this valve is open, the inlet channel 4 is in communication with the pump chamber 24 by the orifice 36 and another orifice 40.

The outlet valve 26 also has a membrane 42 of generally circular form which is without any orifice therein and an annular sealing ring 44 which, as is the case with the inlet valve, is covered with a thin oxide layer. Opening- this outlet valve enables direct communication between the pumping chamber 24 and the outlet channel 6.

Finally, it should be noted that the piezoelectric disc which brings about the variations in volume of the pump chamber, is connected by two electrical conductors 46 and 48 through electrodes (not shown) situated on the faces of the piezoelectric disc to a voltage source 50.

In accordance with the invention the outlet valve 26 is equipped with a position detector. The projection 56 shown on the reverse face (i.e. the side that, in this embodiment, is not in contact with the fluid to be pumped) of the valve as well as the support 32 form part of this detector. Two special embodiments of the detector will now be described.

Figure 3:
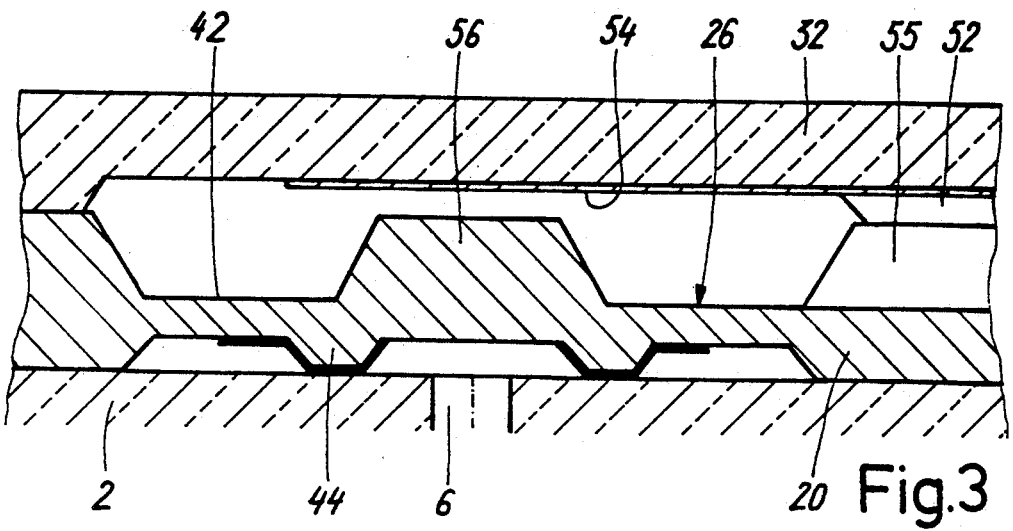
FIGS. 3 and 4 shows in section a valve according to a first embodiment of the invention, in the closed and open positions respectively.
Figure 4:
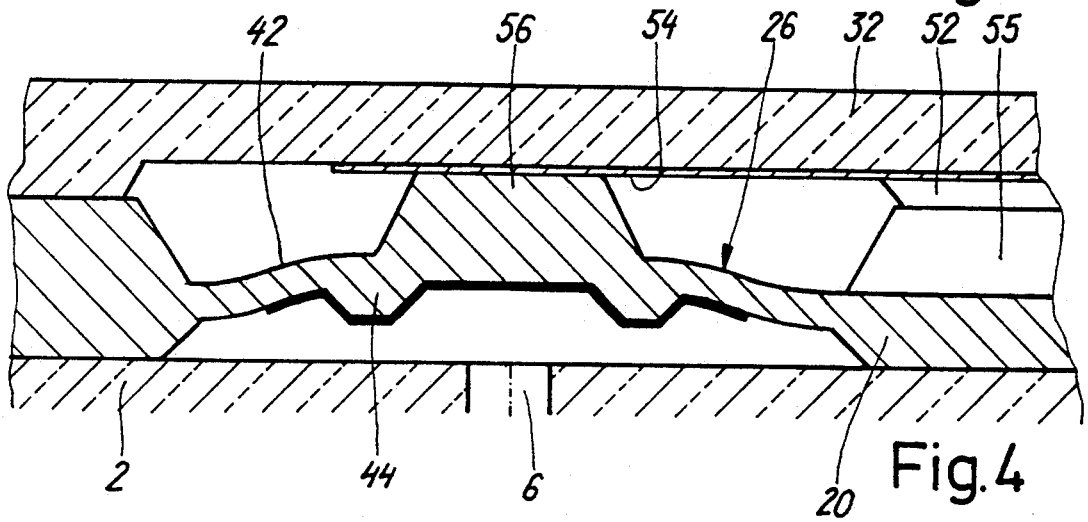
Figure 5:
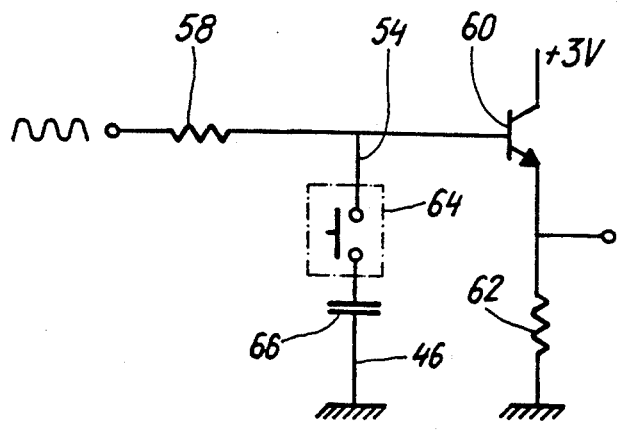
FIG. 5 shows a schematic representation of a detection circuit suitable for use with a valve of FIGS. 3 and 4, FIGS. 6 and 7 show in section a valve according to a second embodiment of the invention, in the closed and open positions respectively.

A first embodiment in which the detector is of the capacity type is shown in FIGS. 3 to 5.

Notice that for good shape control, the effective lateral membrane dimensions are defined by the shallow etching from the front of the valve. Also, here the valve has thermal oxide on the membrane as well. This provides sufficient pre-tension with thin membranes. With thin membranes, the deflection can be large.

The support 32, which may for example be of glass, may have a groove 52 on its face bonded to the wafer 20. An electrode 54 for example of Au, A1 or of Indium-Tin Oxide (ITO) is formed on the support 32. The distance between the electrode 54 and the upper part of the back face of the valve 26, that is to say the surface of the projection 56, is such that there is a mechanical contact between the valve body and the electrode 54 when the valve is in the open position. In order to reduce parasitic capacitance between the electrode 54 and the silicon wafer 20 one may increase the distance between them by also forming a groove 55 in the wafer 20. The upper surface of the projection 56 may be insulated, for example using a thin oxide layer (in the order of 1 µm thickness).

Thus, when the valve 26 is closed (FIG. 3) the distance between the valve and the electrode 54 (the detector gap) is of the order of 5 µm, whereas when the valve 26 is open (FIG. 4) the valve and the electrode are in contact with each other.

The schematic circuit shown in FIG. 5 shows the position of the valve. It comprises a resistor 58 connected on the one hand to an alternating current source and on the other hand to an electrode 54; a transistor 60 of which the collector is connected to a source of direct current at 3 V and the base to the electrode 54; and a resistor 62 place between the emitter of the transistor 60 and ground. The valve 26 acts as switch 64, which according to the device used, may be either of a resistive and/or capacitive nature. The silicon plate 20 is directly connected to the apparatus or, as shown, by way of a conductor 46 of the control circuit of the piezoelectric disc; in this case, the capacitor 66 represents the capacity therebetween.

In this embodiment, the conductor 46 forming one of the electrical contacts is connected to the wafer 20. It could equally well only be connected electrically thereto, for example to form an air capacitor.

A high-frequency signal, for example of 30 KHz (so that the detection signal is sufficiently modulated as a function of the position of the valve, taking into account the impedances of the components and to avoid interference with the control signal of the piezoelectric disc) is applied to the electrode 54 by way of the resistor 58. The signal detected by the emitter of the transistor 60 is a function of the open or closed position of the valve.

The duration of the signal also enables distinction to be made between malfunctioning due to the presence of an air bubble in the pump chamber, which could result in incomplete opening, but also a rapid reclosing of the valve after it had been opened by a signal applied to the piezoelectric disc, and malfunctioning due to elevated pressure in the outlet channel of the micropump resulting in prolonged opening of the valve.

The pump may also be constructed or operated in such a way that during normal pumping the valve does not reach the open position, but only when the pressure on the outlet is too high. In such a case, one takes full advantage of the invention only for detecting a too high outlet pressure or blockage.

A circuit of the passive detection type may also be employed in certain cases. When a control signal is applied to the piezoelectric disc (ca. 130 V DC signal) a short interference signal appears on the emitter of the transistor 60 when the valve is in the open position (FIG. 4). However, this signal is less reproducible. To eliminate this signal, one may add a small capacitor in series with the detection line.

A second embodiment in which the position detector is of the resistor type is shown in FIGS. 6 to 8.

FIGS. 6 and 7 are identical to FIGS. 4 and 5 except that a supplementary electrode 68 is provided on the back face of the valve 26 opposite the electrode 54. This electrode may for example be of Au, Al or Indium-Tin Oxide, and it is connected to a conductor 70 of the same material which is accomodated in groove 52.

A detection circuit is shown schematically in FIG. 8. It comprises a resistor 72 placed between the electrode 54 and a voltage source, for example alternating voltage at 30 kHz. The presence or absence of an alternating voltage on the conductor 54 indicates the open or closed position of the valve. As with the circuit of FIG. 5, detection of the closing of the circuit and measurement of the duration of this closing gives information on the presence and nature of malfunctioning of the micropump.

In the embodiment of FIGS. 6 and 7, one of the electrodes is provided on the back face of the valve. There is a way to avoid an independent forming or deposition of the electrodes; one may simply provide both electrodes on support 32, spaced apart one from the other in such a way that they are both in contact with the valve when the latter is in the open position. Such a structure is shown on FIG. 9a, on which same elements as the ones of FIGS. 6 and 7 bear the same reference numerals. The electrodes 54 and 74 may have a semi-disc shape, as shown on FIG. 9b; the electrical connections are made through grooves (like groove 52 in FIGS. 3 and 6) or through electroplated through holes 76, 78 in support 32.

The detection of the open position of the valve, i.e. when the valve is in contact with the electrodes may be of resistive type or capacitive type. In the latter case, the contact is less critical and has the advantage of a strongly reduced by-pass current through the liquid, compared to the first embodiment.

The micropumps according to the invention are intended to be used notably for the injection of medicaments. Such micropumps require therefore a precise control of the opening and of the closing of the valves. However, while it is relatively easy to control the depth of the etching of the silicon wafer, it is more difficult to control the thickness of the membrane of the valves since the thickness of a silicon wafer is not constant over its whole surface, but on the contrary shows certain variations. The thickness of the membrane governs the amount of pre-tension and hence ultimately the parameters for the opening and the closing of the valves. This is particularly important in the case of the outlet valve which requires a greater pre-tension.

The degree of this pre-tension depends notably on the pre-tension due to the the thickness of the oxide layer on the sealing ring. This pre-tension corresponds to the third power of membrane thickness. It is added to the pre-tension which is caused by, for example, an oxide layer on the membrane and which also depends on the membrane thickness, but there only to the first power. In this conventional case, a too thick a membrane will cause an increase in both the pre-tension due to the oxide on the sealing ring, and in the pre-tension due to the oxide on the membrane. The variation of the overall pre-tension is the sum of both pre-tension variations. The pre-tension caused by the oxide on the sealing ring can play an important role in this variation, due to the third order variation.

FIG. 10 shows a fourth embodiment of the invention in which the pre-tension is less dependant on the membrane thickness, and in which an additional etching step to obtain this is used to provide all or part of the detector gap 53. By way of example, the detector is of capacitive type, as in the embodiment of FIGS. 3 to 5, with the electrode 54 on support 32 being connected to the detector circuit via an electroplated through hole 76 provided in support 32. In this embodiment there has been etching of the sealing ring in a additional etching step (during which the membrane may also been etched, and in this case has been etched and that on both sides) and the oxide layer on it is less thick than the depth of the etching, so that the effective thickness of the sealing ring is less than its nominal thickness. Thus if there is oxide on the sealing ring only, and not on the membrane, the sealing ring will not come into contact with the valve seat. In the same way as in the conventional case, it is clear that the sealing ring creates a pre-tension, now a negative one, whose absolute value is equal to the pressure which would have been exerted on the membrane for the sealing ring to be flush with the valve seat. But in this case an oxide layer is also formed on the membrane (oxide layer can be provided on one side of the membrane or, as shown in FIG. 10., on both sides), the pre-tension to which the valve is subjected will be equal to the pre-tension caused by the curvature of the membrane diminished by this negative pretension. In this situation, the variation in the membrane oxide pretension is approximatively compensated by the variation in the negative sealing ring gap pre-tension.

The dimensions are chosen so that the overall pretension remains substantially constant for a certain range of membrane thicknesses. Moreover, the dimensions may be chosen such as to match the required detector gap with the additional etching in order to obtain the required gap with the same additional etching step. In this example, the projection 56 is thereto etched as well, simultaneously.

Simulations have shown that micropumps equipped with an outlet valve according to the embodiment of FIG. 10 show substantially the same pre-tension and thus nearly the same behaviour despite differences of ±2.5 μm in the membrane thickness of the valves having a mean thickness of 25 μm (depth of sealing ring etching approximatively 4 μm; oxide layer approximatively 1 μm thick).

The position detector according to the invention has the following properties:
- no mechanical calibration is necessary since the detector only has to distinguish between two values of the signal which correspond respectively to the open and closed positions (or incomplete opening) of the valve,
- insensitive to interference with exterior signals (for example a control signal for the piezoelectric disc),
- simple, inexpensive components and fabrication.

In relationship to the embodiments described above, it may be added that the position detector of the capacitive type (FIGS. 3 to 5) functions in a satisfactory manner even if there is not a good electrical contact between the valve and the electrode 54, whereas the electric circuits of the detector of the resistive type (FIGS. 6 to 8, and 9a, 9b) is particularly simple.

What is claimed is:

1. A micropump comprising a first wafer; at least a second wafer mounted on said first wafer to define a pump chamber; means for causing said pump chamber to take in and drive out a fluid; a valve located downstream from said pump chamber and having a valve body and a valve seat facing the front of the valve body; and a valve position detector having a first electrical contact facing the back of the valve body at such a distance that there is a mechanical contact between the valve body and said first electrical contact when the valve is in the open position and said mechanical contact is absent when said valve is in the closed position, a second electrical contact disposed such that it forms an electrical impedance with said first electrical contact, which is influenced by said mechanical contact, and detection means sensitive to the electrical impedance between said electrical contacts for providing an output signal representative of a duration of said mechanical contact capable of indicating a malfunction of the micropump.

2. A valve according to any of claim 1, wherein in that said second electrical contact is fixed to said first wafer.

3. A micropump according to claim 2, wherein second electrical contact is a second electrode placed opposite the first electrical contact, the detection means being sensitive to the electrical resistance between said electrical contacts.

4. A micropump according to claim 2, in which said first wafer is of a semiconductor material, wherein said second electrical contact is connected to said first wafer and conductively insulated from said first electrical contact and wherein the detection means is sensitive to the electrical capacitance between said electrical contacts.

5. A micropump according to any one of claim 1, wherein in that the means comprises an alternating current generator.

6. A micropump according to claim 1, wherein said first wafer is machined to form said pump chamber and said valve body, and wherein said second wafer is mounted on said first wafer to form said valve seat.

7. A micropump according to claim 6 wherein said valve has a membrane and a sealing ring, at least the membrane being provided with a layer inducing a pre-tension keeping the valve in the closed position, in the absence of external influence, and at least the sealing ring being so machined that, if the membrane layer would be omitted, the valve would be in the open position in the absence of external influence.

8. A micropump according to claim 7, in which a detector gap (53) is machined by etching of the valve body, characterized in that said machining is done simultaneously with, and at least partially by, said machining of the sealing ring.

9. A micropump according to claim 6, a support is mounted on said first wafer facing the back face of the valve body, said support accomodating said first electrical contact.

10. A micropump according to claim 6 wherein the back face of the valve comprises a projection opposite said first electrical contact.

11. A micropump according to any one of claim 9, wherein in that said second electrical contact is provided on said support, faces the back face of the valve body and is electrically isolated from said first electrical contact.

12. A micropump according to claim 1, wherein said detection means comprises a detection circuit and means for applying a high-frequency input signal to said detection circuit.

13. A micropump comprising a first wafer; a second wafer, said first wafer being machined so as to define, with at least the second wafer mounted face to face on the first wafer, a pump chamber; an inlet valve by means of which said pump chamber can selectively communicate with an inlet of the micropump; an outlet valve by means of which said pump chamber can communicate with an outlet of the micropump, said outlet valve having a valve body and a seat facing the front of the valve body; means for inducing a periodic variation in the volume of said pump chamber; and an outlet valve position detector having a first electrical contact facing the back of the valve body at such a distance that there is a mechanical contact between the valve body and said first electrical contact when the outlet valve is in the open position and said mechanical contact is absent when the outlet valve is in the closed position, a second electrical contact disposed such that it forms an electrical impedance with said first electrical contact, which is influenced by said mechanical contact, and detection means sensitive to the electrical impedance between said electrical contacts for providing an output signal representative of a duration of said mechanical contact capable of indicating a malfunction of the micropump.

14. A micropump according to claim 13, wherein the back face of the outlet valve comprises a projection opposite said first electrical contact.

15. A micropump according to claim 13, wherein said first wafer is machined to form said pump chamber and said outlet valve body, and wherein said second wafer is mounted on said first wafer to form said outlet valve seat.

16. A micropump according to claim 15, wherein said second electrical contact is fixed to said first wafer.

17. A micropump according to claim 16 wherein the second electrical contact is a second electrode placed opposite the first electrical contact, the detection means being sensitive to the electrical resistance between said electrical contacts.

18. A micropump according to claim 17 wherein said outlet valve has a membrane and a sealing ring, at least the membrane being provided with a layer inducing a pre-tension keeping the outlet valve in the closed position in the absence of external influence, and at least the sealing ring being so machined that, if the membrane layer would be omitted, the outlet valve would be in the open position in the absence of external influence.

19. A valve according to claim 16 wherein said first wafer is of a semiconductor material, wherein said second electrical contact is connected to said first wafer and conductively insulated from said first electrical contact and wherein the detection circuit is sensitive to the electrical capacitance between said electrical contacts.

20. A micropump according to claim 19 wherein said outlet valve has a membrane and a sealing ring, at least the membrane being provided with a layer inducing a pre-tension keeping the outlet valve in the closed position in the absence of external influence, and at least the sealing ring being so machined that, if the membrane layer would be omitted, the outlet valve would be in the open position in the absence of external influence.

21. A micropump according to claim 15 wherein a support is mounted on said first wafer facing the back face of the outlet valve body, wherein said support accommodates said first electrical contact, and wherein said second electrical contact is provided on said support, faces the back face of the valve body and is electrically isolated from said first electrical contact.

22. A micropump according to claim 15 wherein said outlet valve has a membrane and a sealing ring, at least the membrane being provided with a layer inducing a pre-tension keeping the outlet valve in the closed position in the absence of external influence, and at least the sealing ring being so machined that, if the membrane layer would be omitted, the outlet valve would be in the open position in the absence of external influence.

23. A micropump according to claim 13, wherein said detection means comprises a detection circuit and means for applying a high-frequency input signal to said detection circuit.

* * * * *

UNITED STATES PATENT AND TRADEMARK OFFICE
CERTIFICATE OF CORRECTION

PATENT NO. : 5,271,724

DATED : December 21, 1993

INVENTOR(S) : Harald T.G. van Lintel

It is certified that error appears in the above-identified patent and that said Letters Patent is hereby corrected as shown below:

Column 7, line 6, change "valve" to --micropump--; same line, change "any of claim 1" to --claim 6--, and delete "in";
    line 7, delete "that";
    line 9, after "wherein" insert --the--;
    line 14, change "in which" to --wherein--;
    line 21, delete "any one of";
    line 22, delete "in that", and after "the" insert --detection--;
    line 36, delete "(53)";
    line 37, change "characterized in that" to --and--;
    line 40, after "6," insert --wherein--;
    line 44, change "6" to --1,--; and
    line 47, delete "any one of".

Signed and Sealed this

Sixteenth Day of August, 1994

Attest:

BRUCE LEHMAN

Attesting Officer      Commissioner of Patents and Trademarks